(12) United States Patent
Kantrowitz

(10) Patent No.: US 8,383,407 B2
(45) Date of Patent: *Feb. 26, 2013

(54) PERCUTANEOUS ACCESS DEVICE SYSTEM FACILITATING CELL GROWTH THEREON

(75) Inventor: Allen B. Kantrowitz, Williamstown, MA (US)

(73) Assignee: L-VAD Technology, Inc., Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/372,025

(22) Filed: Feb. 13, 2012

(65) Prior Publication Data

US 2012/0150149 A1   Jun. 14, 2012

Related U.S. Application Data

(62) Division of application No. 11/460,339, filed on Jul. 27, 2006, now Pat. No. 7,704,225.

(60) Provisional application No. 60/703,661, filed on Jul. 29, 2005.

(51) Int. Cl.
    *C12N 5/071* (2010.01)
(52) U.S. Cl. ............... 435/396; 435/402; 435/366
(58) Field of Classification Search ............ None
    See application file for complete search history.

(56) References Cited

U.S. PATENT DOCUMENTS

| 3,663,965 A | 5/1972 | Lee, Jr. et al. |
| 3,906,549 A | 9/1975 | Bucalo |
| 3,964,470 A | 6/1976 | Trombley |
| 3,995,644 A | 12/1976 | Parsons |
| 4,183,357 A | 1/1980 | Bentley et al. |
| 4,321,914 A | 3/1982 | Begovac et al. |
| 4,634,422 A | 1/1987 | Kantrowitz et al. |
| 4,668,222 A | 5/1987 | Poirier |
| 4,676,802 A | 6/1987 | Tofield et al. |
| 4,897,081 A | 1/1990 | Poirier et al. |
| 5,242,415 A | 9/1993 | Kantrowitz et al. |
| 6,031,148 A | 2/2000 | Hayes et al. |
| 6,039,714 A | 3/2000 | Cracauer et al. |
| 7,704,225 B2 * | 4/2010 | Kantrowitz .............. 604/43 |
| 2003/0224032 A1 | 12/2003 | Read et al. |
| 2004/0170663 A1 | 9/2004 | Wang et al. |
| 2005/0080338 A1 | 4/2005 | Sirimanne et al. |
| 2005/0181011 A1 | 8/2005 | Hunter et al. |

OTHER PUBLICATIONS

Control of Cellular Organization in Three Dimensions Using a Microfabricated Polydimethylisiloxane-Collagen Composite Tissue Scaffold; Mar. 2005, vol. 11, No. 3-4: 378-386.

* cited by examiner

*Primary Examiner* — Jim Ketter

(74) *Attorney, Agent, or Firm* — Patent Procurement Services

(57) ABSTRACT

A process to facilitate growing of cells on a nanotextured percutaneous portal is provided that includes the placement of a nanotextured percutaneous portal partially within a subject. A vacuum manifold is secured to the nanotextured percutaneous portal. Upon coupling the vacuum manifold to a vacuum source, the growth of the cells is facilitated.

7 Claims, 1 Drawing Sheet

PERCUTANEOUS ACCESS DEVICE SYSTEM FACILITATING CELL GROWTH THEREON

CROSS-REFERENCE TO RELATED APPLICATIONS

This application is a divisional application of U.S. patent application Ser. No. 11/460,339 filed Jul. 27, 2006, which claims priority of U.S. Provisional Patent Application 60/703,661 filed Jul. 29, 2005, these applications are incorporated herein by reference.

FIELD OF THE INVENTION

The present invention in general relates to percutaneous access devices and in particular to a percutaneous access device amenable to skin growth around the device periphery so as to form a biologically stable seal.

BACKGROUND OF THE INVENTION

A common problem associated with implantation of a percutaneous access device (PAD) is skin regeneration about the periphery of the device to form an immunoprotective seal against infection. New cell growth and maintenance is typically frustrated by the considerable mechanical forces exerted on the interfacial layer of cells. In order to facilitate skin regeneration about the exterior of a PAD, subject cells are often harvested and grown in culture onto PAD surfaces for several days prior to implantation in order to allow an interfacial cell layer to colonize PAD surfaces in advance of implantation. Unfortunately, cell culturing has met with limited acceptance owing to the need for a cell harvesting surgical procedure preceding the implantation procedure. Additionally, maintaining tissue culture integrity is also a complex and time-consuming task.

As an alternative to cell culturing on a percutaneous access device, vacuum assisted wound treatment about a percutaneous access device has been attempted. While Dacron based random felt meshes have been used to promote cell regrowth in the vicinity of a wound, such felts have uncontrolled pore sizes that harbor bacterial growth pockets.

Thus, there exists a need for a percutaneous access device surface and processes to enhance autologous cell growth into a stable long term relation to the device.

SUMMARY OF THE INVENTION

A biocompatible implantable portal is provided that has a wall defining a communicative passage through an interior bore. The exterior of the portal has a neck region adapted to promote autologous cell growth on the neck region. A series of channels are provided on the exterior neck region to facilitate autologous cell growth while disfavoring fluid pooling and bacterial growth. Typical channel widths are from 20 to 300 microns, with adjacent channels being separated by plateaus having a width of between 0 and 600 microns. Providing the portal exterior neck region with a texture varying on a nanometer length scale facilitates autologous cell growth. Applying a coating such as a tissue scaffolding matrix to the neck region prior to implantation also facilitates cell growth. A coupling or a manifold encompassing the neck region facilitates the draw of vacuum and/or mechanical protection for the growing cells.

By forming a seal between a manifold encompassing the neck region of a portal to form a seal and providing a route of fluid communication between the manifold inlet and channels associated with the portal exterior, various gaseous or liquid fluids are provided to enhance cell growth after implantation of a percutaneous access device is facilitated.

A process is provided for producing a biocompatible implantable portal having a nanoporous surface. The process includes dispersing nanocrystals in a polymer to yield a polymer dispersion. The polymer dispersion is applied onto the surface of a portal. Exposing the polymer dispersion on the surface to a solution selectively dissolves the nanocrystals from the surface to create the nanoporous surface. An alternative process includes forming a dual domain coating having a first domain type and a second domain type dispersed through the coating on the portal. Selectively removing the first domain type leaves the material of the second domain type in place to yield the porous surface.

DETAILED DESCRIPTION OF THE INVENTION

Figure 1:
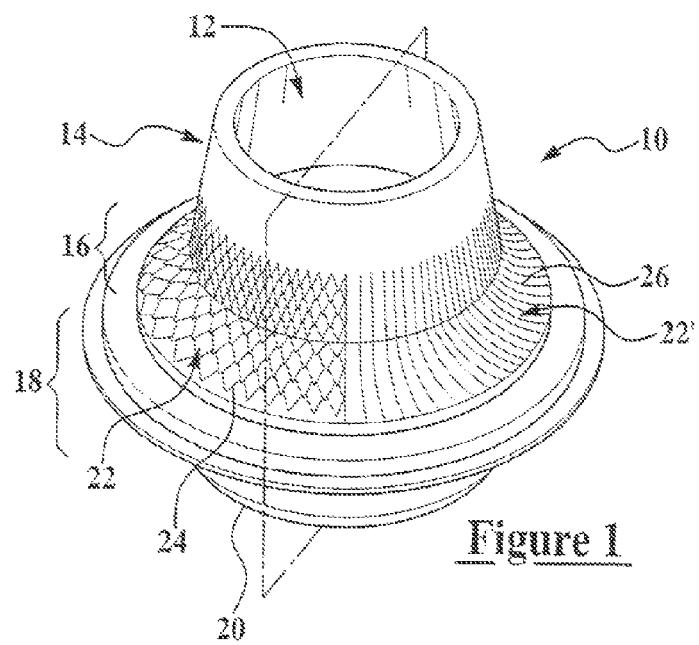
FIG. 1 is a composite perspective view depicting two exemplary cell growth channel pattern halves to an inventive percutaneous access device joined together where the cell growth channels are not depicted to scale for visual clarity.

The present invention has utility as a protective assembly for a portal for the coupling of a permanent or semi-permanent medical intervention, the portal having an interior bore through which communication is maintained between the portal recipient and external medical equipment. As a result, the conveyance of electrical signals, pneumatic drive power, or biological fluids is facilitated. Such portals are routinely used in conjunction with mechanical auxiliary ventricles, chronic ambulatory peritoneal dialysis, prosthetic limb anchorage to an amputation stump, cochlear or other neurological stimulators, drainage tubes, and vascular access lines as exemplary of instances in which such a portal is used. Exemplary of such portals are those detailed in U.S. Pat. Nos. 4,634,422; 4,668,222; 5,059,186; 5,120,313; 5,250,025; 5,814,058; 5,997,524; and 6,503,228. Such devices are collectively defined herein as percutaneous access devices (PADs).

The stabilization of a PAD within the skin to form a germ-free barrier requires subject cells to grow onto the neck surfaces of the PAD adjacent to the subject's epidermis. The present invention uses alone, or in combination cell channeling contours, porous biodegradable polymers and the application of vacuum to promote cellular growth towards the surface the neck of a PAD. The present invention in facilitating rapid cellular colonization of a PAD neck allows the subject to act as their own cell culture facility and as such affords more rapid stabilization of the PAD, and lower incidence of separation and infection.

Referring now to the figures, an inventive portal is shown generally at 10. The portal 10 has an opening 12 defined by a sidewall 14 the exterior side of the wall 14 defining a neck region 16 adapted to promote growth of autologous fibroblast cells thereon. A suitable exterior side surface substrate for fibroblast growth is a nanotextured polycarbonate (LEXAN) as detailed as a sleeve in U.S. Pat. No. 4,634,422. Unfortunately, the process of fission product bombardment followed by etching in a base solution detailed yields a range of pits and pores that vary in size to an extent that some of the pores are large enough to harbor pools of extracellular fluid and bacteria. A preferred method of generating a nanotextured neck surface yields pore sizes that are uniformly less than 500 to provide an anchor point for a fibroblast podocyte, while having dimensions that disfavor bacterial colonization. More preferably, a nanotextured surface as used herein has a uniform distribution of 50 to 500 nanometer median dimension indentations. Most preferably, the indentations have a median dimension of between 100 and 300 nanometers.

A method of forming such pores in a ceramic or metal neck involves impregnating a porous polymer such as a polyurethane with particulate and combusting the polymer under conditions that allow the particles to sinter to form a porous surface with the desired properties. U.S. Pat. No. 4,004,933 details such a process. An analogous porous polymeric neck is formed by forming an interpenetrating polymer network in which the two networks are not cross linked. Exposing the resultant structure to a condition such as a solvent digestive towards only one type of interpenetrating polymer network domain yields a porous surface. It is appreciated that the domain need not be uniform in dimension. By way of example, the second domain type remaining after digestion or dissolution of the first domain type is formed as globular, spherical or other shape that is present at or above the percolation threshold such that these second domains are cross linked, sintered or otherwise adhered to yield a porous surface coating. Representative second domain types operative herein illustratively include metals, ceramics, and polymeric beads.

Alternatively, combustion of a polymer containing metal or ceramic ions or inclusions yields a porous coating of the second domain type of the metal, the metal oxide or ceramic. Polyacrylic acid and polycarbonate are representative of water soluble and organic solvent polymers, respectively.

Alternatively, an acid etchable, biocompatible nanocrystal such as silver or silica is dispersed in a polymer melt such as polycarbonate and a neck either formed directly therefrom or the nanocrystal-doped polymer is coated onto a neck substrate. Through subjecting the nanocrystal-doped polymer to an acid or base solution, depending on the solubility of the nanocrystal, voids are formed in the polymer reflective of the original nanocrystal dopant. For instance, silver is readily dissolved in 6 N hydrochloric acid while silica is dissolved in concentrated hydrofluoric acid. Dissolution in the presence of sonication is appreciated to facilitate the process. Silver represents a preferred nanocrystal as nanocrystal leachant not dissolved imparts antimicrobial properties to the resulting neck. Nanocrystal loading of 1 to 10 percent by weight, depending on the specific nanocrystal dimensions, is sufficient to achieve the desired uniformity and density of pores.

Beneath the neck region 16 lies an implanted region 18 terminating in an inward portal face 20, that is communicative with the opening 12 to form a passage through which fluids, electrical signals, gases or a combination thereof are communicated. The neck region 16 has a pattern of contoured autologous cell-conveying channels 22 or 22'.

It is appreciated that the channels can take a variety of forms. In the figures, a linear channel 24 and a chrysanthemum-pattern channel 26 are depicted in composite halves as defined by the dashed plane. It is appreciated that an operative device typically would have a pattern 24 or 26 circumferentially decorating the device surface. Other channel patterns operative herein include any pattern that disfavors bacterial pocket formation. Specific patterns operative herein are those associated with vehicle tire treads with the proviso that sharp angular interactions between channel and intermediate plateaus are disfavored. Representative of these patterns are those found in U.S. Pat. No. 5,896,905. The channel 22 is formed by methods such as imprinting, embossing, molding or machining into the portal 10. Preferably, the portal 10 is a nanotextured surface as detailed in regard to the sleeve in U.S. Pat. No. 4,634,422. As a portal 10 is formed of a conventional biocompatible material, one of skill in the art will appreciate the relative merits of impressing, embossing, machining, or molding based on whether the portal 10 is formed of a metal such as stainless steel, or titanium; a thermoplastic such as a fluoropolymer (TEFLON), a polyoxymethylene (DELRIN), or polycarbonate (LEXAN); or composite material. A channel 22 according to the present invention preferably has dimensions on the order of two to ten times the diameter of a plasma-borne fibroblast that is equivalent to 20 to 300 microns since a fibroblast has a diameter from 10 to 15 microns. More preferably, an inventive channel 22 has a width of between 30 and 120 microns. Most preferably, channel 22 is devoid of discontinuities and acute angles that disfavor cellular planarization and adhesion. A parabolic cross section is exemplary of a channel facilitating fibroblast growth. Typically, the plateau region between adjacent channels 22 has a width ranging from 0 to 600 microns. Preferably, the transition between the channel 22 and the plateau 30 is devoid of discontinuities and acute angles that disfavor cellular planarization and adhesion. A non-existent zero micron width plateau 30 corresponds to the instance where the cross section between channels corresponds to a sinusoidal pattern or the edges of adjacent parabolic channels intersect. Preferably, a plateau 30 has a width relative to an adjacent channel width that defines a ratio between 0.5 and 3:1. The alternation of channels 22 and plateaus 30 according to the present invention facilitates capillary draw of fibroblasts up into the neck region 16 of the inventive device 10.

Optionally, the neck region 16 is coated with a substance to facilitate cellular infiltration and growth on the neck region 16. Such coating substances include cell growth scaffolding matrices as detailed in U.S. Pat. Nos. 5,874,500; 6,056,970; and 6,656,496; and Norman et al. *Tissue Eng.* 3/2005, 11(3-4) pp. 375-386. Preferably, autologous plasma from the subject receiving an inventive portal 10 is applied to the neck region 16 as part of a scaffold matrix or independent thereof. More preferably, the coating 32 is porous in order to enhance capillary draw. More preferably, the coating 32 is porous and biodegradable. The coating has pores typically of an average size of between 10 and 500 microns, and preferably, of an average size of between 30 and 50 microns.

Optionally, a vacuum is drawn toward an upward region of the neck region 16 in order to actively draw blood plasma and fibroblasts contained therein along the channels 22 to further facilitate autologous cell growth on the neck region 16. Preferably, vacuum is applied intermittently for the first days or weeks after PAD implantation. The length of time for which vacuum is applied is dependent upon variables illustratively including vacuum strength, linear dimension of the neck region to be colonized, channel pattern, porosity characteristics of any coating present, subject wound fluid production, and subject serum fibroblast concentration.

Figure 2:
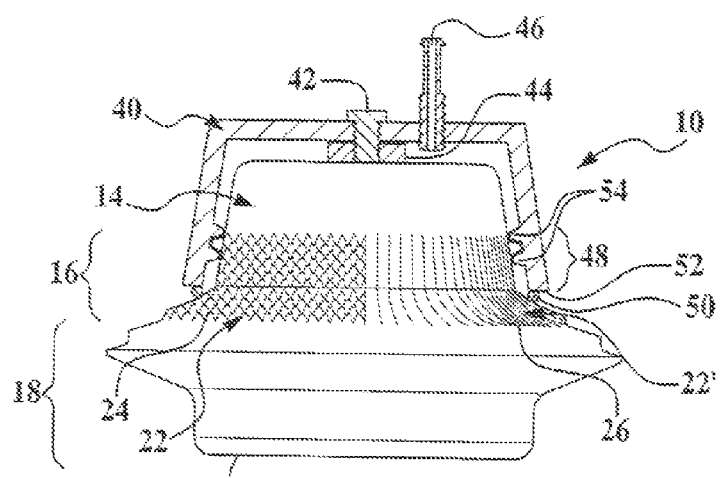
FIG. 2 is a plan view of the percutaneous access device depicted in FIG. 1 with a cross-sectional view along with a cross-sectional view of a vacuum manifold coupled thereto.
Figure 3:
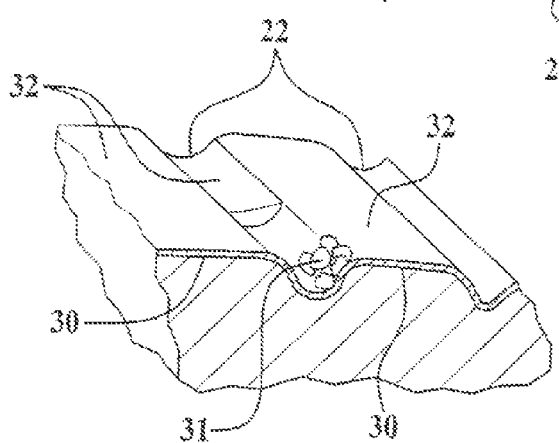
FIG. 3 is a perspective view of a cell growth channel according to the present invention.

Referring now to FIG. 2, a vacuum manifold 40 is secured to an inventive portal 10 by way of a fastener 42. The fastener 42 extends into a temporary seating pin (not shown) to fit within the opening 12. A spacer 44 assures a uniform gap between the manifold 40 and the neck region 16. An inlet 46 is provided for the coupling of the manifold 40 to a vacuum source. Manifold 40 has an extending lip 48 that terminates proximal to a surface of the neck portion 16 at least one point amenable to form a seal 50 with the surrounding subject skin or a gel applied to the user skin. It is appreciated that a retaining groove 54 is defined on a lip surface in opposition to the portal neck portion 16, the retaining groove 54 amenable to seat a vacuum gasket between the manifold 40 and the neck portion 16. A gasket used herein is formed of conventional materials illustratively including neoprene. While the skin seal 50 is suitable to draw a vacuum around the periphery of the neck portion 16, cells that are drawn within the portal portion under vacuum tend to be drawn to a surface of the neck portion 16 as opposed to intercalating within a channel or a matrix coating. As such, it is appreciated that while drawing a vacuum at the interface between the neck portion 16 and lip terminus 52 is suitable to urge an initial population of cells into the channels 22, drawing of cells to the uppermost reaches of channels 22 preferably occurs by forming a vacuum seal between the manifold 40 and the neck portion 16 that includes only the uppermost terminus of the channels 22. It is appreciated that once cells 31 begin to adhere to a surface defining a portion of a channel 22 or plateau 30, abrasion and indeed contact with that surface is preferably avoided. It is further appreciated that a retaining groove 54 and the ensuing vacuum seal formed between the manifold 40 and the neck portion 16 is readily moved relative to the neck portion 16 by varying the thickness of the spacer 44. While the manifold 40 is beneficial in drawing serum and the fibroblasts contained therein through the channels 22 in the neck portion 16, it is also appreciated that independent of vacuum, the manifold 40 also serves to provide a mechanical guard to protect growing cells on the neck portion 16. To this end, it is appreciated that an inlet 46 can be connected to a gas supply such as air or oxygen to promote autologous cell growth and granulation about the neck portion 16; or liquid solutions fostering cell growth are also provided and illustratively include autologous plasma, fibroblast growth enhancing solutions, and antimicrobials.

A vacuum source suitable for coupling to the inlet 46 includes conventional vacuum sources such as a mechanical pump, aspirator, peristaltic pump, and the pneumatic system of a left ventricular assist device of a system such as the Kantrowitz CARDIOVAD drive unit as detailed at lvadtech-.com. Optionally, a fibroblast compatible dye (not shown) is placed in proximity to channel termini nearest the implanted region 18, the dye serving as a marker to indicate the extent of capillary draw of cells 31 into channels 22 and the optionally present coating 32.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process to facilitate growing of cells on a nanotextured percutaneous portal comprising: placing the nanotextured percutaneous portal partially within a subject; securing a vacuum manifold to the nanotextured percutaneous portal; and coupling said vacuum manifold to a vacuum source to facilitate the growing of the cells.

2. The process of claim 1 wherein said vacuum source is one of mechanical pump, aspirator, peristaltic pump, or a pneumatic system.

3. The process of claim 1 further comprising coating the nanotextured percutaneous portal with an autologous cell growth promoter coating.

4. The process of claim 3 wherein said coating is a tissue scaffolding matrix.

5. The process of claim 4 wherein said tissue scaffolding matrix comprises autologous fibroblasts.

6. The process of claim 3 wherein said coating is porous.

7. The process of claim 6 wherein said porous coating has an average pore size of between 30 and 500 microns.

* * * * *